(12) United States Patent
Baucom

(10) Patent No.: US 8,658,628 B2
(45) Date of Patent: Feb. 25, 2014

(54) HORMONE DELIVERY SYSTEM AND METHOD

(76) Inventor: Karan Y. Baucom, Overland Park, KS (US)

(*) Notice: Subject to any disclaimer, the term of this patent is extended or adjusted under 35 U.S.C. 154(b) by 539 days.

(21) Appl. No.: 12/818,798

(22) Filed: Jun. 18, 2010

(65) Prior Publication Data
US 2010/0324006 A1    Dec. 23, 2010

Related U.S. Application Data

(60) Provisional application No. 61/218,301, filed on Jun. 18, 2009.

(51) Int. Cl.
*A61K 31/56* (2006.01)

(52) U.S. Cl.
USPC ............................... 514/170; 514/182

(58) Field of Classification Search
USPC .................................. 514/182, 170
See application file for complete search history.

(56) References Cited

U.S. PATENT DOCUMENTS

| | | | |
|---|---|---|---|
| 4,382,441 A | 5/1983 | Svedman | |
| 4,534,468 A | 8/1985 | Nuckols et al. | |
| 4,573,606 A | 3/1986 | Lewis et al. | |
| 4,816,258 A | 3/1989 | Nedberge et al. | |
| 4,900,734 A * | 2/1990 | Maxson et al. | 514/171 |
| 5,091,182 A | 2/1992 | Ong et al. | |
| 5,288,479 A | 2/1994 | Gorman et al. | |
| 5,300,302 A | 4/1994 | Tachon et al. | |
| 5,310,082 A | 5/1994 | Coustenoble | |
| D352,458 S | 11/1994 | Gray | |
| 5,397,776 A | 3/1995 | DeLuca et al. | |
| 5,505,959 A | 4/1996 | Tachon et al. | |
| 5,609,270 A | 3/1997 | Walker | |
| 5,813,785 A | 9/1998 | Baudin et al. | |
| 5,897,539 A | 4/1999 | Elliesen et al. | |
| 5,922,349 A | 7/1999 | Elliesen et al. | |
| 5,927,548 A | 7/1999 | Villaveces | |
| 5,958,446 A | 9/1999 | Miranda et al. | |
| 6,083,528 A | 7/2000 | Elliesen et al. | |
| 6,098,835 A | 8/2000 | DeJonge | |
| 6,165,491 A | 12/2000 | Grasset et al. | |
| 6,228,852 B1 | 5/2001 | Shaak | |
| 6,507,275 B2 | 1/2003 | Romano et al. | |
| D473,786 S | 4/2003 | Chue | |
| 6,544,553 B1 | 4/2003 | Hsia et al. | |
| 6,561,389 B1 | 5/2003 | Earle | |
| 6,581,797 B2 | 6/2003 | McKinney, Jr. et al. | |
| 6,866,865 B2 | 3/2005 | Hsia et al. | |
| 6,967,194 B1 | 11/2005 | Matsuo et al. | |
| 7,100,797 B2 | 9/2006 | Kahn et al. | |
| 7,101,106 B1 | 9/2006 | Wiley | |
| 7,186,706 B2 | 3/2007 | Rosario-Jansen | |
| 7,204,391 B2 | 4/2007 | Toker | |
| D543,120 S | 5/2007 | Coe et al. | |
| 7,449,310 B2 | 11/2008 | Nagaraja et al. | |
| 2008/0226703 A1 | 9/2008 | Sacks et al. | |

OTHER PUBLICATIONS

"Take comfort in her protection", brochure: *Micronized Prometrium Progesterone, USP*—retrieved Mar. 16, 2009.
Schwartz, Erika et al., "The Truth About Hormone Therapy", Retrieved online Mar. 16, 2009: http://online.wsj.com, 2.
"BioResponse DIM Offers Superior Safety, Stability, Dosage and Efficacy", Retrieved online Jun. 18, 2010: www.bioresponse.com, 3.
Mead, Jay H., Retrieved online May 26, 2010: www.labrix.com, (1 of 1).
"Risks and Benefits of Estrogen Plus Progestin in Healthy Postmenopausal Women: Principal Results From the Women's Health Initiative Randomized Controlled Trial", *Writing Group for the Women's Health Initiative Investigators; Journal of the American Medical Association*, Jul. 17, 2002; vol. 288, No. 3, pp. 321-333.
Gelfand, et al., "Abstract of Clinical Assessment and Quality of Life of Postmenopausal Women Treated With a New Intermittent Progestogen Combination Hormone Replacement Therapy: A Placebo-Controlled Study", *Menopause*. Jan. 2003, vol. 10, Issue 1, pp. 29-36.
Google, "Google image search for "graphs on the menstrual cycle"", https://www.google.com/search?noj=1&q=graphs%20on%20the%20menstrual%20cycle&um=1&ie=UTF-8&hl=en&tbm=isch&source=og&sa=N&tab=wi&ei=F68XUtrlHqW42AWCjoGgCw&biw=1440&bih=770&sei=Ga8XUtG4F6ed2gXzyoCoCQ.
Holtorf, Kent "Abstract of the Bioidentical Hormone Debate: Are Bioidentical Hormones (Estradiol, Estriol, and Progesterone) Safe or More Efficacious then Commonly Used Synthetic Versions in Hormone Replacement Therapy?", *Postgraduate Medicine*, vol. 121, Issue 1, Jan. 2009.
L'Hermite, et al., "Could Transdermal Estradiol + Progesterone Be a Safer Postmenopausal HRT? A Review.", *Maturitas*, vol. 60 (2008), pp. 185-201.
North American Menopause Society, "Estrogen and Progestogen Use in Postmenopausal Women: 2010 Position Statement of the North American Menopause Society", *Menopause*. Mar. 2010, 17(2), pp. 242-255.

(Continued)

*Primary Examiner* — San-Ming Hui
(74) *Attorney, Agent, or Firm* — Law Office of Mark Brown, LLC; Mark E. Brown; Christopher M. DeBacker

(57) ABSTRACT

A hormone delivery system and method are provided for administering bio identical human hormones using a combination of modalities for the treatment of human physiological conditions.

6 Claims, No Drawings

(56) References Cited

OTHER PUBLICATIONS

North American Menopause Society, "Recommendations for Estrogen and Progestogen Use in Peri- and Postmenopausal Women: Oct. 2004 Position Statement of the North American Menopause Society", *Menopause.* vol. 11, No. 6. pp. 589-600.

Novogyne Pharmaceuticals, "Dialogues in Menopause Management", (Jan. 2012).

Oger, et al., "Differential Effects of Oral and Transdermal Estrogen/Progesterone Regimens on Sensitivity to Activated Protein C Among Postmenopausal Women: A Randomized Trial." *Arterioscler Thromb Vasc Biol.*, Sep. 1, 2003, 23(9). pp. 1671-1676.

Scarabin, et al., "Effects of Oral and Transdermal Estrogen/Progesterone Regimens on Blood Coagulation and Fibrinolysis in Postmenopausal Women: A Randomized Controlled Trial", *Arterioscler Thromb Vasc Biol.* 1997; 17: pp. 3071-3078.

Spencer, et al., "Effects of Oral and Transdermal 17B-Estradiol With Cyclical Oral Norethindrone Acetate on Insulin Sensitivity, Secretion, and Elimination in Postmenopausal Women", *Metabolism*, vol. 49, No. 6, Jun. 2000, pp. 742-747.

Vashisht, et al., "A Study to Look at Hormonal Absorption of Progesterone Cream Used in Conjunction with Transdermal Estrogen", *Gynecological Endocrinology*, 2005, vol. 21(2), pp. 101-105.

Whitehead, et al., "Absorption and Metabolism of Oral Progesterone", *British Medical Journal*, Mar. 22, 1980, pp. 825-827.

Wikipedia, "Menstrual Cycle Definition", http://en.wikipedia.org/wiki/Menstrual_cycle.

\* cited by examiner

HORMONE DELIVERY SYSTEM AND METHOD

CROSS-REFERENCE TO RELATED APPLICATIONS

This application claims priority in U.S. Provisional Patent Application No. 61/218,301, filed Jun. 18, 2009, which is incorporated herein by reference.

BACKGROUND OF THE INVENTION

1. Field of the Invention

The present disclosed technology relates generally to the administration of human hormones, and in particular to various delivery methods of bioidentical hormone formulations.

2. Description of the Related Art

Hormones are chemical substances produced by cells and organs of the body that affect organs and body systems. Hormones are important for cardiovascular maintenance, musculature, the skeletal system, and cognitive functioning. The body's production of hormones and how the body reacts to hormones affect the well being of individuals and the aforementioned body systems.

The body has three general categories of sex hormones; androgens (ex. testosterone), estrogens (estradiol and estrone), and progestagens (ex. progesterone). Particular female sex hormones and their associated organs are, for example, testosterone (ovaries), estrone and estradiol (ovaries), and progesterone (ovaries and placenta). Testosterone promotes the growth and maintenance of the skeletal system, musculature, and connective tissues, to name a few. Estradiol and estrone principally affect the female reproductive system. Progesterone affects the female menstrual cycle, and maintenance of pregnancy. Hormone deficiencies caused by aging, disease states, exogenous and endogenous environmental conditions, and certain prescribed medications can upset the balance of sex hormones within the body and affect general well being, lifespan, quality of life, and may lead to disease states as well. Therefore, in order to counter the negative effects of hormone deficiencies, patients are often prescribed hormone replacement therapy (HRT) by their treating physicians.

HRT is a system of treatment using either synthetic sex hormones, or bioidentical sex hormones to treat the effects of diminished sexual hormone levels in perimenopausal, menopausal, and postmenopausal women. Synthetic sex hormones are the predominant type of hormone proscribed in HRT. The types of techniques used in HRT to deliver sex hormones includes pills, capsules, gels, creams, patches and troches. Use of synthetic sex hormones in HRT comes with significant problems such as heart problems, cancers and other undesirable side effects. Furthermore, the type and amount of sex hormone administered is limited by dosing regimes associated with the available delivery techniques. Patient selection of desired delivery techniques and source of sex hormones will increase the effectiveness of therapy and compliance. Moreover, the ability of a physician to tailor the amount of sex hormone delivered with each dosing regime will increase the effectiveness of HRT. Therefore, there is a need for a system of HRT that avoids the undesirable side-effects of synthetic hormone treatments, and that provides the patient with a range of techniques for administering the hormones to maximize well being and maintenance of body systems.

Heretofore there has not been available a hormone delivery system with the advantages and features of the disclosed technology.

SUMMARY OF THE INVENTION

A hormone delivery system is disclosed providing for administration of bioidentical human hormones using a combination of modalities for the treatment of human physiological conditions where treatment by hormone therapy is indicated. Bioidentical estrogen, progesterone and androgen preparations may be administered individually, or in combination to a patient using one or more modalities such as transdermal absorption or ingestion. The hormone delivery system can be used to treat pre-menstrual tension syndrome, peri-menopause, menopause, post-menopause, progesterone deficiency, estrogen dominance, libido issues, and birth control.

DETAILED DESCRIPTION OF THE PREFERRED EMBODIMENTS

I. Introduction and Environment

As required, detailed aspects of the disclosed technology are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art how to variously employ the disclosed technology in virtually any appropriately detailed structure.

II. Embodiment or Aspect of the Hormone Delivery System

The hormone delivery system embodying the principles of the disclosed technology provides for administration of compositions containing bioidentical human hormones in an amount sufficient to provide therapeutic effect, using a combination of modalities, for the treatment of human physiologic conditions. Examples of specific bioidentical hormones which may be used include, but are not limited to estrogens (estrone, estradiol), progesterone, and androgens (testosterone, androstenedione, dihydrotestosterone (DHT), dehydroepiandrosterone (DHEA)) isomers and derivatives thereof, and combinations thereof. Examples of specific modalities which may be used include, but are not limited to topical preparations (gel, cream), ingested articles (tablet, lozenge, capsule, troches), and articles for transdermal absorption of hormone preparations (transdermal patch, impregnated matrices). The type and amount of hormones involved in the various bioidentical human hormone compositions, and the modalities used varies depending independently, or in conjunction with, the physiologic sequence based on the normal menstrual cycle pattern, and specific clinical syndromes involved. A single bioidentical hormone, or a combination of bioidentical hormones may be used with any particular modality.

The hormone delivery system may be used for the treatment of conditions related to hormone imbalances or deficiencies where treatment by hormone therapy is indicated. For example, the types of conditions for which the hormone delivery system nay be used include, but are not limited to: pre-menstrual tension syndrome; peri-menopause, menopause, post-menopause; progesterone deficiency; estrogen dominance; and libido issues. In conjunction with treatments using estrogens, the hormone delivery system is used in conjunction with indole-3-carbinol, di-indole methane, or flax seed to protect biochemically from hydroxylation of estrogen.

III. Alternative Embodiment or Aspect of the Hormone Delivery System

A hormone delivery system comprising another embodiment or aspect of the disclosed technology can be used for birth control. The bioidentical human hormones estrogens (estrone, estradiol), progesterone using a combination of modalities mentioned above are administered to a patient in a sequential format following the human physiological twenty-eight day menstrual cycle. Any combination of patches, capsules and other types of delivery systems can be utilized, provided the menstrual cycle is simulated.

Various combinations of estrogen/progesterone can be administered as a cream with suitable proportions and dosage ranges.

IV. Conclusion

It will be appreciated that the components of the hormone delivery system can be used for various other applications. Moreover, the hormone delivery system can be fabricated in various sizes and from a wide range of suitable materials, using various manufacturing and fabrication techniques.

By way of example and without limitation, estrogen can be administered as a patch, gel or cream in suitable dosages of, for example, 0.25 mg, 0.375 mg, 0.5 mg, 0.75 mg and 1.0 mg. Progesterone can be administered as a patch, gel, cream, capsule or sublingual in suitable dosages of, for example, 25 mg, 50 mg, 75 mg, 100 mg, 200 mg and 300 mg. Di-indole methane/3-indole carbinol (Dim/3IC) can be administered as 400 mg tablets or gels. However, estrogen-dominant patients should only be given progesterone during days 1-25 of their menstrual cycles. If any estrogen is used, an option is to utilize 3IC/Dim for pathway protection for increasing 2-meo/2 hydroxylation excretion. It is generally important for the patient to excrete estrogen.

It is to be understood that while certain aspects of the disclosed technology have been shown and described, the disclosed technology is not limited thereto and encompasses various other embodiments and aspects.

Having thus described the invention, what is claimed as new and desired to be secured by Letters Patent is:

1. A method of delivering hormones to a patient, which method comprises the steps of:
   providing a predetermined quantity of human hormones;
   determining a hormone deficiency in the patient;
   matching a hormone with the determined hormone deficiency;
   delivering progesterone and estrogen to the patient in a sequential format following the human physiological twenty-eight day menstrual cycle using a modality comprising transdermal absorption; and
   thereby treating hormone imbalances or deficiencies associated with peri-menopause, menopause and post-menopause.

2. The method of claim 1, which includes the additional step of:
   treating pre-menstrual tension syndrome.

3. The method of claim 1, which includes the additional step of:
   treating progesterone deficiency.

4. The method of claim 1, which includes the additional step of:
   treating estrogen dominance.

5. The method of claim 1, which includes the additional step of:
   treating libido deficiencies.

6. The method of claim 1, which includes the additional steps of:
   providing birth control by administering bioidentical human hormones to a patient in a sequential format following the human physiological twenty-eight day menstrual cycle.

\* \* \* \* \*